United States Patent
Mabuchi et al.

(10) Patent No.: US 6,334,946 B1
(45) Date of Patent: Jan. 1, 2002

(54) METHOD OF STABILIZING PUMP CURRENT IN GAS SENSOR

(75) Inventors: Tomohiro Mabuchi, Aichi; Shigeki Mori, Gifu; Satoshi Teramoto; Takeshi Kawai, both of Aichi, all of (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/321,568

(22) Filed: May 28, 1999

(30) Foreign Application Priority Data

May 28, 1998 (JP) .................................................. 10-147854

(51) Int. Cl.$^7$ ..................................................... G01N 27/41
(52) U.S. Cl. ...................... 205/784; 205/784.5; 204/402; 204/425; 204/426
(58) Field of Search ..................................... 204/924, 425, 204/426, 427, 428, 429, 402; 205/783.5, 784, 784.5; 73/23.32

(56) References Cited

U.S. PATENT DOCUMENTS

| | | |
|---|---|---|
| 3,843,400 A | 10/1974 | Radford et al. |
| 3,978,006 A | 8/1976 | Topp et al. |
| 4,283,441 A | 8/1981 | Haecker et al. |
| 4,498,968 A | 2/1985 | Yamada et al. |
| 4,683,049 A * | 7/1987 | Nakajima ...................... 204/428 |
| 4,767,520 A * | 8/1988 | Asakura et al. ............... 204/406 |
| 4,842,711 A * | 6/1989 | Asakura et al. ............... 204/406 |
| 4,863,583 A * | 9/1989 | Kurachi et al. ............... 204/424 |
| 5,338,431 A * | 8/1994 | Yorita et al. .................. 204/424 |
| 5,804,699 A * | 9/1998 | Sugiyama et al. ............ 73/23.32 |
| 5,866,799 A * | 2/1999 | Kato et al. .................... 204/425 |

FOREIGN PATENT DOCUMENTS

| | | |
|---|---|---|
| EP | 0 294 085 | 12/1988 |
| JP | 52-30699 | 8/1977 |
| JP | 55-78246 | 6/1980 |
| JP | 59-24382 | 6/1984 |
| JP | 59-178354 | 10/1984 |
| JP | 63-300955 | 12/1988 |

OTHER PUBLICATIONS

Logothetis et al "High–Temperature Oxygen Sensors Based on Electrochemical Oxygen Pumping", Fundamentals and Applications of Chemical Sensors, pp. 136–154, Month Unavail. 1986.*

* cited by examiner

*Primary Examiner*—Robert J. Warden, Sr.
*Assistant Examiner*—Kaj K. Olsen
(74) *Attorney, Agent, or Firm*—Sughrue Mion, PLLC

(57) ABSTRACT

A method of stabilizing pump current in a gas sensor through suppression of oscillations of the pump current which result from pulsations of measured gas is provided. The gas sensor includes an oxygen pump element, an oxygen concentration cell element and a measurement gap between the oxygen pump element and the oxygen concentration cell element, and is operative to control the pump current through the oxygen pump element so that an output voltage of the oxygen concentration cell element is constant in order that an oxygen concentration in the measurement gap is maintained constant and detect an oxygen concentration in the measured gas on the basis of the pump current. The method comprising adjusting an activity of electrodes of an oxygen pump element so as to change a responsiveness in control of the pump current and thereby reduce an amplitude of the oscillations of the pump current. There is also provided the above described type gas sensor wherein the activity of the electrodes of the oxygen pump element is adjusted so as to change a responsiveness in control of the pump current and thereby reduce the oscillations of the pump current.

2 Claims, 5 Drawing Sheets

METHOD OF STABILIZING PUMP CURRENT IN GAS SENSOR

BACKGROUND OF THE INVENTION

1. Field of the Invention

The present invention relates to gas sensors, particularly a gas sensor adapted to control pump current through an oxygen pump element so as to hold the output voltage of an oxygen concentration cell element at a constant value and measure the oxygen concentration in measured gas on the basis of the pump current. More particularly, the present invention relates to a method of stabilizing pump current in a gas sensor through control of oscillations of the pump current which result from pulsations of measured gas.

2. Description of the Related Art

One of gas sensors heretofore known as an oxygen sensor, includes an oxygen concentration cell element made up of a pair of porous electrodes and an oxygen ion conductive solid electrolyte base interposed between the electrodes, and an oxygen pump element, the oxygen concentration cell element and the oxygen pump element being laid one upon another.

Such an oxygen sensor has a diffusion or measurement gap between the above described two elements. The measurement gap is in communication with a measured gas side by way of a diffusion control layer. By controlling current through the oxygen concentration cell element so that the output voltage of the oxygen concentration cell element is maintained at a predetermined constant value, the oxygen concentration in the measurement gap is controlled to a constant value. In this instance, the pump current through the oxygen pump element is proportional to the oxygen concentration in the measured gas, so that measurement of the oxygen concentration can be attained on the basis of that current value.

Such an oxygen sensor is attached to an exhaust pipe of a vehicle for instance and used for measuring the oxygen concentration in the exhaust gas (i.e., air-fuel ratio). In the exhaust pipe, the exhaust gas pulsates at cyclic intervals at which the engine performs its exhaust stroke. When the exhaust gas pulsates, the absolute quantity of oxygen varies depending upon variations of the density of the exhaust gas. Thus, the pump current through the oxygen sensor is influenced by the exhaust gas pulsations and caused to oscillate in the same cycle as the exhaust gas pulsations.

In the meantime, in the pump current control, there is a time lag causing a variation of the pump current after the output voltage is detected by the oxygen concentration cell element. Thus, depending upon an oscillation cycle of the pump current (i.e., the pulsation cycle of the exhaust gas), there may occur a hunting in the control, thus causing the pump current to oscillate at a larger amplitude than that to otherwise result from the actual oscillations. When the pump current is in such an oscillating condition, there arises a problem that accurate detection of the oxygen concentration cannot be attained on the basis of the pump current.

Another problem is that if such hunting occurs at the time of fuel cut where the oxygen concentration in the exhaust gas is increased to cause relatively large current to flow through the oxygen pump element, excessively large current flows through the oxygen pump element to deteriorate the oxygen pump element.

SUMMARY OF THE INVENTION

It is accordingly an object of the present invention to provide a method of stabilizing pump current in a gas sensor through suppression of oscillations of the pump current which result from pulsations of measured gas.

It is another object of the present invention to provide an oxygen gas sensor which is obtained by the above method.

To achieve the foregoing objects, the present invention provides a method of stabilizing pump current in a gas sensor through suppression of oscillations of the pump current which result from pulsations of measured gas. The gas sensor includes an oxygen pump element and an oxygen concentration cell element, each of which has a pair of porous electrodes containing a catalyst for accelerating a reaction between a solid electrolyte and oxygen and an oxygen ion conductive solid electrolyte base interposed between the electrodes. The gas sensor further includes a measurement gap between the oxygen pump element and the oxygen concentration cell element and in communication with a measured gas side by way of a diffusion control layer, and is operative to control the pump current through the oxygen pump element so that an output voltage of the oxygen concentration cell element is constant in order that an oxygen concentration in the measurement gap is maintained constant and detect an oxygen concentration in the measured gas on the basis of the pump current. The method comprises adjusting an activity of the electrodes of the oxygen pump element so as to change a responsiveness in control of the pump current and thereby reduce the oscillations of the pump current.

The present invention also provides a gas sensor comprising an oxygen pump element and an oxygen concentration cell element, each of which has a pair of porous electrodes containing a catalyst for accelerating a reaction between a solid electrolyte and oxygen and an oxygen ion conductive solid electrolyte base interposed between the electrodes, the gas sensor further comprising a measurement gap between the oxygen pump element and the oxygen concentration cell element and in communication with a measured gas side by way of a diffusion control layer, and operative to control the pump current through the oxygen pump element so that an output voltage of the oxygen concentration cell element is constant in order that an oxygen concentration in the measurement gap is maintained constant and detect an oxygen concentration in the measured gas on the basis of the pump current, wherein an activity of the electrodes of the oxygen pump element is adjusted so as to change a responsiveness in control of the pump current and thereby reduce an amplitude of the oscillations of the pump current.

DETAILED DESCRIPTION OF THE PREFERRED EMBODIMENT

Figure 1A:
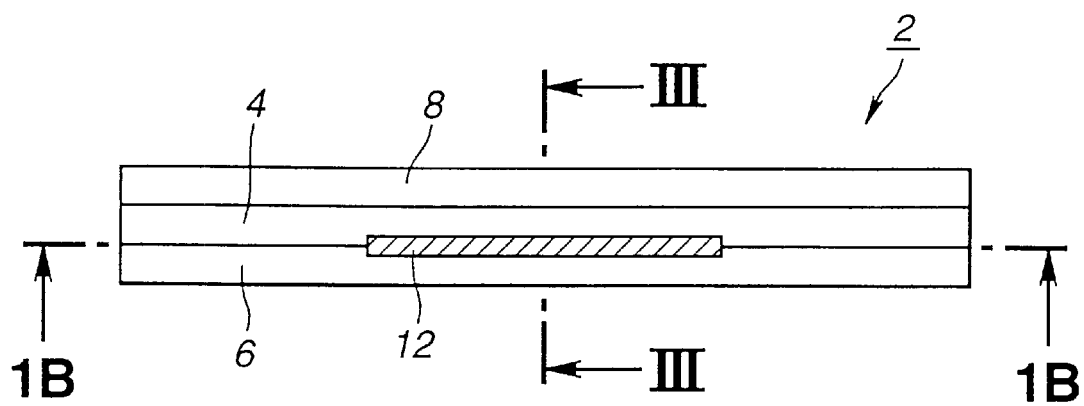
FIG. 1A is a side elevational view of an oxygen sensor.
Figure 1B:
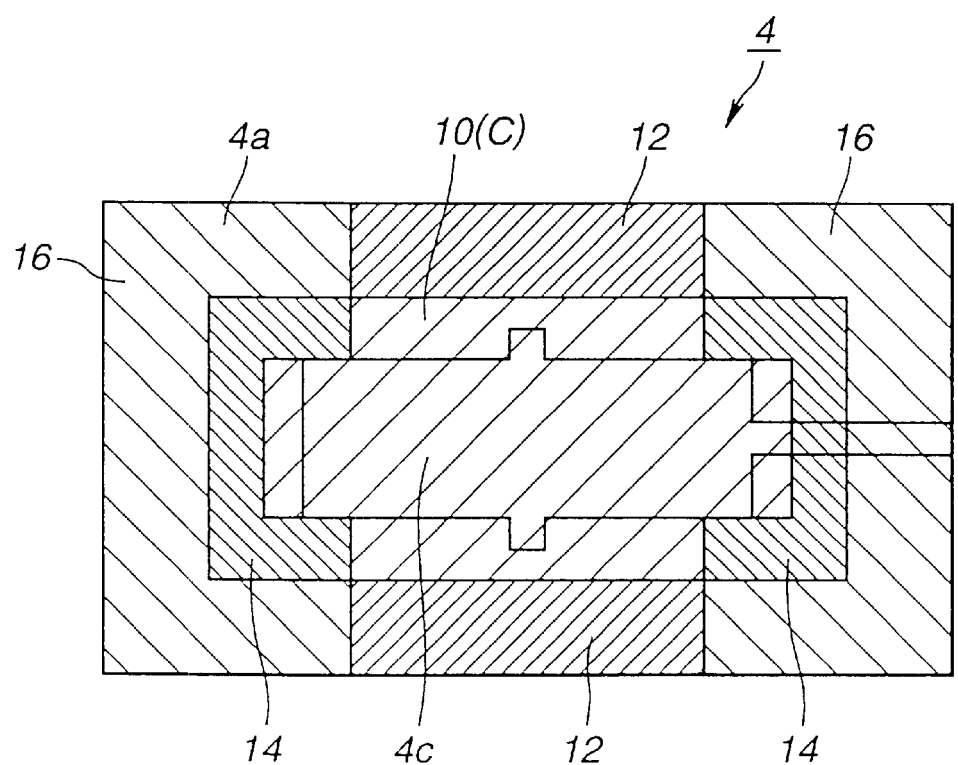
FIG. 1B is a sectional view taken along the line IB—IB of FIG. 1A.
Figure 2:
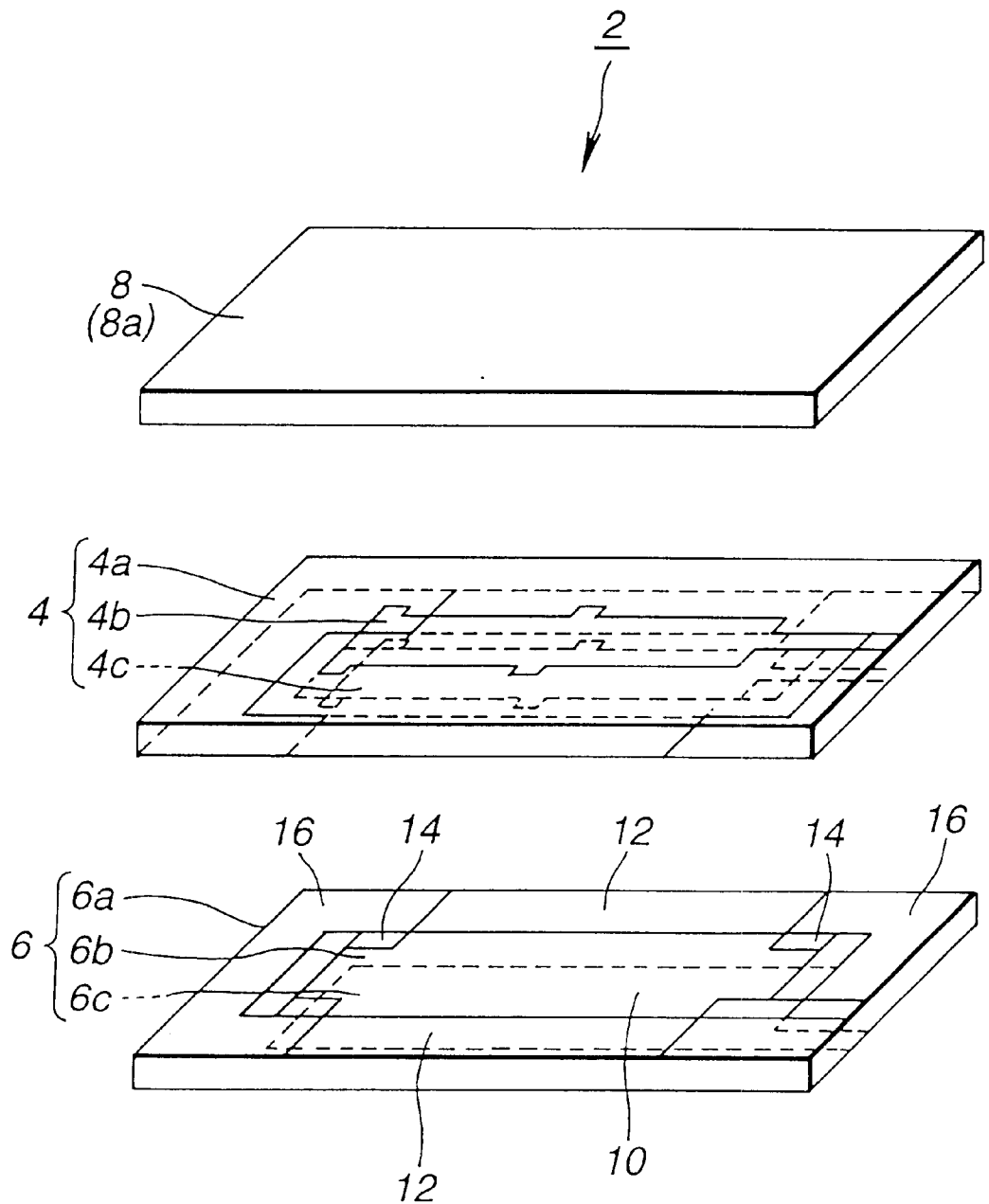
FIG. 2 is an exploded view of the oxygen sensor of FIG. 1A.
Figure 3:
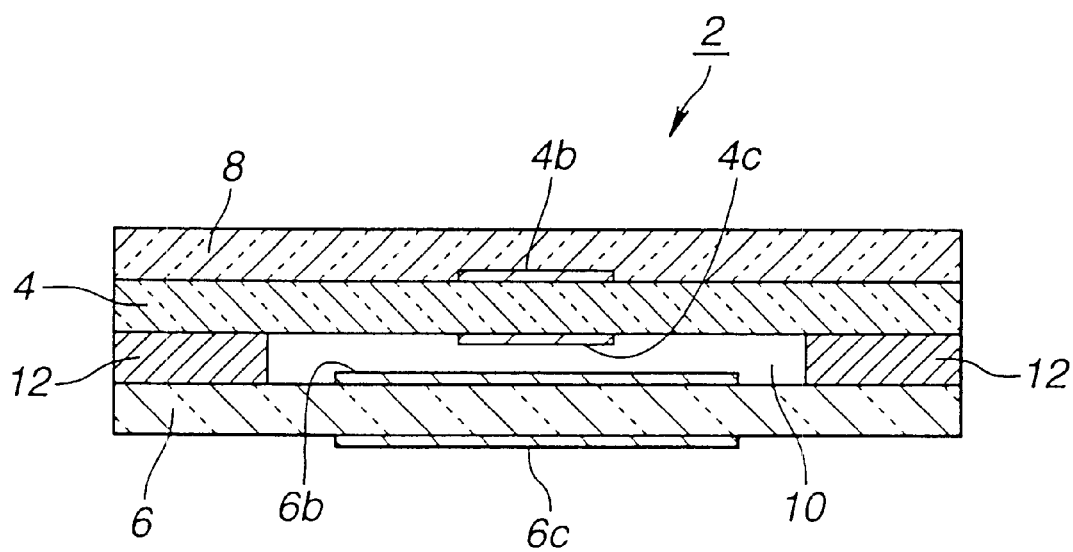
FIG. 3 is an enlarged sectional view taken along the line III—III of FIG. 1A.

Referring to FIGS. 1A–1B to 3, an oxygen sensor according to an embodiment of the present invention is generally designated by 2. The oxygen sensor 2 is adapted to be attached to an exhaust system of an automotive vehicle for instance and used for detecting an oxygen concentration (i.e., air/fuel ratio) in exhaust gas (i.e., measured gas) over a wide range, i.e., the oxygen sensor 2 is used as a wide-range air/fuel ratio sensor.

The oxygen sensor 2 includes an oxygen concentration cell element 4 made up of a solid electrolyte base 4a and a pair of porous electrodes 4b and 4c disposed on the opposite sides of the solid electrolyte base 4a, an oxygen pump element 6 made up of a solid electrolyte base 6a and a pair of porous electrodes 6b and 6c disposed on the opposite sides of the solid electrolyte base 6a, and a shield 8 made up of a solid electrolyte base 8a. The oxygen concentration cell element 4, the oxygen pump element 6 and the shield 8 are laminated in such a manner as to interpose the oxygen concentration cell element 4 between the oxygen pump element 6 and the shield 8. The oxygen concentration cell element 4 and the oxygen pump element 6 differ a little in the shape of the porous electrodes.

At the interface between the oxygen concentration cell element 4 and the oxygen pump element 6, there are provided a diffusion or measurement gap 10 (inner hatched portion in FIG. 1B), a pair of diffusion control layers 12 for communicating therethrough the measurement gap 10 with the outside space (i.e., measured gas side), a pair of buffer layers 14, and a pair of insulation layers 16. The electrode 4c of the oxygen concentration cell element 4 and the electrode 6b of the oxygen pump element 6 are disposed within the measurement gap 10 in a way as to be opposite to each other. The diffusion control layers 12 are disposed at the ends of the measurement gap 10 which are opposed in the direction crossing at right angles the longitudinal direction thereof. The buffer layers 14 are provided so as to be in contact with the peripheral portion of the measurement gap 10 except for the peripheral portion in contact with the diffusion control layers 12. The insulation layers 16 cover a side surface of the solid electrolyte base 6a other than the portion thereof provided with the measurement gap 10, the diffusion control layers 12 and the buffer layers 14.

In the meantime, any of the solid electrolyte bases 4a, 6a and 8a which respectively constitute the oxygen concentration cell element 4, oxygen pump element 6 and shield 8 is made of an oxygen ion conductor containing a solid solution of zirconia ($ZrO_2$). The porous electrodes 4b, 4c, 6b and 6c of the oxygen concentration cell element 4 and the oxygen pump element 6 are made of a porous material which includes for its major constituent platinum and has a catalytic function for accelerating a chemical reaction of oxygen and solid electrolyte. Further, the diffusion control layers 12 and the buffer layers 14 covering the peripheral portion of the measurement gap 10 are made up of a porous body of alumina ($Al_2O_3$), whereas the insulation layer 16 is made up of a dense body of alumina ($Al_2O_3$).

The shield 8 is provided for preventing oxygen which is pumped into the porous electrode 4b side when small current is caused to flow from the porous electrode 4b side to the porous electrode side 4c of the oxygen concentration cell element 4, from being discharged directly therefrom. Further, the oxygen concentration cell element 4 is formed with a leak-resisting portion (not shown) for allowing a portion of the oxygen pumped into the porous electrode 4b side to leak to the measurement gap 10. This is for allowing the porous electrode 4b side to serve as an oxygen concentration reference source where the oxygen concentration is constant.

The oxygen concentration cell element 4 produces an electromotive force proportional to the ratio between the oxygen concentration on the porous electrode 4b side (i.e., shield 8 side) and the oxygen concentration on the porous electrode 4c side (i.e., measurement gap 10 side). Thus, by maintaining the oxygen concentration on the porous electrode 4b side constant, it is made possible for the oxygen concentration cell element 4 to produce a voltage proportional to the oxygen concentration in the measurement gap 10. By permitting pump current to flow through the oxygen pump element 6 in such a manner that the output voltage of the oxygen concentration cell element 4 is constant, i.e., the oxygen concentration in the measurement gap 10 is constant, the pump current can be proportional to the oxygen concentration in the measured gas flowing into the measurement gap 10, so it becomes possible to detect the oxygen concentration (i.e., air/fuel ratio) on the basis of the pump current.

Then, description will be made to the process for making the oxygen sensor 2 structured as above. The process includes the following steps ① to ⑤.

① Green sheets for forming the solid electrolyte bases 4a, 6a and 8a are prepared by a known doctor blade technology and by using a powder of yttria-zirconia ($Y_2O_3$—$ZrO_2$), a PVB (polyvinyl butyral) binder such as ethyl cellulose and an organic solvent such as toluene.

The green sheet to be formed into the solid electrolyte base 8a of the shield 8 needs not be treated by the following steps ② to ④.

② A Pt powder and $Y_2O_3$—$ZrO_2$ powder are mixed together with a PVB binder and an organic solvent and formed into a smooth paste. By using this paste, patterns of the porous electrodes 4b, 4c, 6b and 6c are screen printed on the above described green sheets.

③ An alumina ($Al_2O_3$) powder is mixed with a PVB binder and an organic solvent similarly to the step ② until a smooth paste is obtained. By using the paste, patterns of the diffusion control layers 12 and the insulation layers 16 are screen printed on the green sheet on which the electrode patterns had been printed.

④ Carbon is applied to a green sheet portion inside of the patterns of the diffusion control layers 12 and the buffer layers 14 having been printed onto the green sheet at the step ③, i.e., a green sheet portion where the measurement gap 10 is to be formed.

In the meantime, by the step ② are processed all of the green sheets which are to be formed into the solid electrolyte bases 4a and 6a of the oxygen concentration cell element 4 and the oxygen pump element 6. By the steps ③ and ④ is processed one of the green sheets which are to be formed into the solid electrolyte bases 4a and 6a.

⑤ Finally, three kinds of green sheets which are formed by the steps ① to ④ are laminated in accordance with the positional relationship described hereinbefore, pressed together, and sintered, for example, at the temperature of 1500° C. for about one hour, whereby to obtain the oxygen sensor 2 of this embodiment.

By sintering, the porous electrodes 4b, 4c, 6b and 6c, the diffusion control layers 12 and the buffer layers 14 are formed into porous bodies, whereas the insulation layers 16 are formed into dense (i.e., nonporous) bodies. The carbon C burns out to form at the place where the carbon C had been applied, a space which constitutes the measurement gap 10 (refer to FIG. 3).

Various pastes can be used for forming the porous electrodes (hereinafter such pastes are referred to as Pt electrode materials). For example, a Pt electrode material called S-22 is a paste of S-powder (granular Pt powder), containing 22% by weight of $Y_2O_3$—$ZrO_2$ powder, SM-14 is a paste of S/M powder (Pt powder obtained by mixing granular Pt powder and Pt powder of fine or small grain size), containing 14% by weight of $Y_2O_3$—$ZrO_2$ powder, and S/M-11 is a paste of S/M powder, containing 11% by weight of $Y_2O_3$—$_{ZrO2}$ powder.

The activities of the porous electrodes made of those electrode materials are, when coparison is made by way of example among S-22, S/M-14 and S/M-11, such that S-22 is largest and S/M-11 is smallest (i.e., S-22>S/M-14>S/M-11).

Figure 4A:
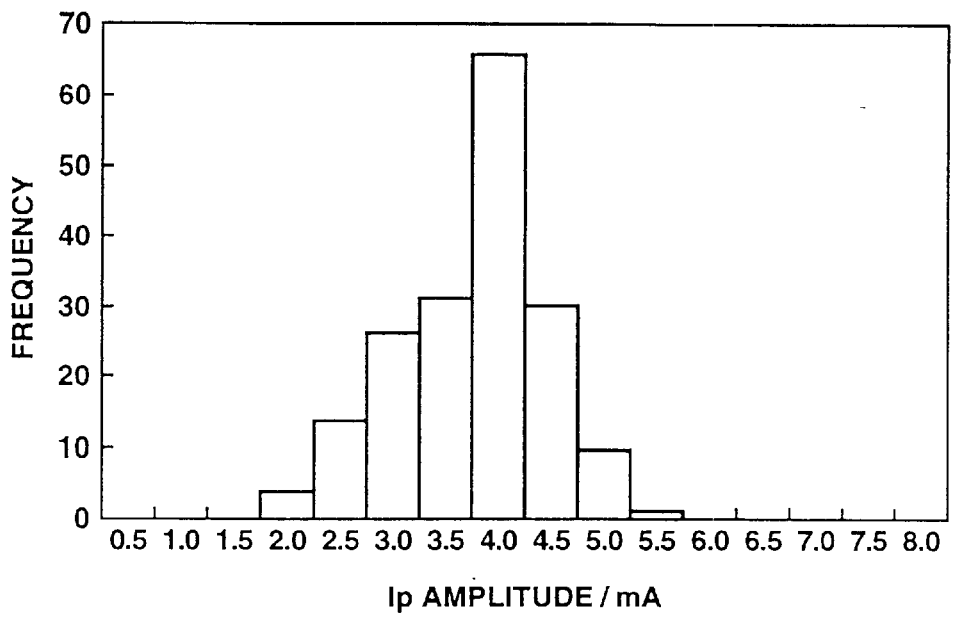
FIGS. 4A and 4B are histograms of the maximum amplitude of oscillations of pump current under different conditions.
Figure 4B:
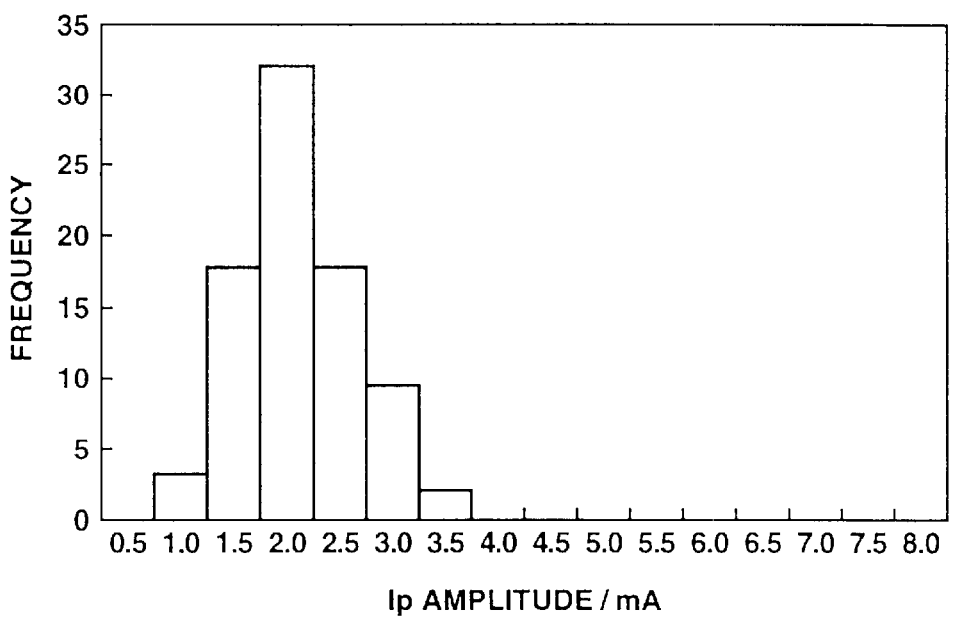

For measurement of the maximum amplitude of oscillations of pump current IP, a 1.5-liter 4-cylinder gasoline engine was used. Under the condition in which the engine was operating at the speed of 2300 rpm, supply of fuel to the engine was cut off. The maximum amplitude of oscillations of pump current Ip during the time from the cutting off of fuel till the engine speeds was reduced to 1000 rpm was measured. The result of measurement was shown in FIGS. 4A and 4B. FIGS. 4A and 4B are histograms showing a frequency distribution of the result of measurement which was carried out with respect to a number of separate articles or examples. The graduation "m" of the axis of abscissa is adapted to represent the frequency of measurement values which are included within the range of m$-0.5 \leq$m$\leq$m$+0.5$ [mA].

As shown in table 1, the materials used for forming the electrodes 4b, 4c, 6b and 6c in case of FIG. 4A were S/M-11, S/M-14, S-22 and S-22, respectively (hereinafter referred to as condition 1), and in case of FIG. 4B S/M-11, S/M-14, S/M-14 and S-22, respectively (hereinafter referred to as condition 2). Namely, the condition 2 is modified so that only the porous electrode 6b of the oxygen pump element 6 which is located on the measurement gap side is adapted to lower in its electrode activity. Except for this, the condition 2 is exactly the same as the condition 1.

TABLE 1

|  |  | CONDITION 1 | CONDITION 2 |
|---|---|---|---|
| OXYGEN PUMP ELEMENT | ELECTRODE 6c | S-22 | S-22 |
|  | ELECTRODE 6b | S-22 | S/M-14 |
| OXYGEN CONCENTRATION CELL ELEMENT | ELECTRODE 4c | S/M-14 | S/M-14 |
|  | ELECTRODE 4b | S/M-11 | S/M-11 |

Under the condition 1, the maximum amplitude of oscillations of the pump current Ip distributes in the range from 2.0 to 5.5 mA, and the most of it is 4.0 mA as seen from FIG. 4A. On the other hand, under the condition 2, the maximum amplitude of oscillations of the Ip current distributes in the range from 1.0 to 3.5 mA, and the most of it is 2.0 mA as seen from FIG. 4B.

Figure 5A:
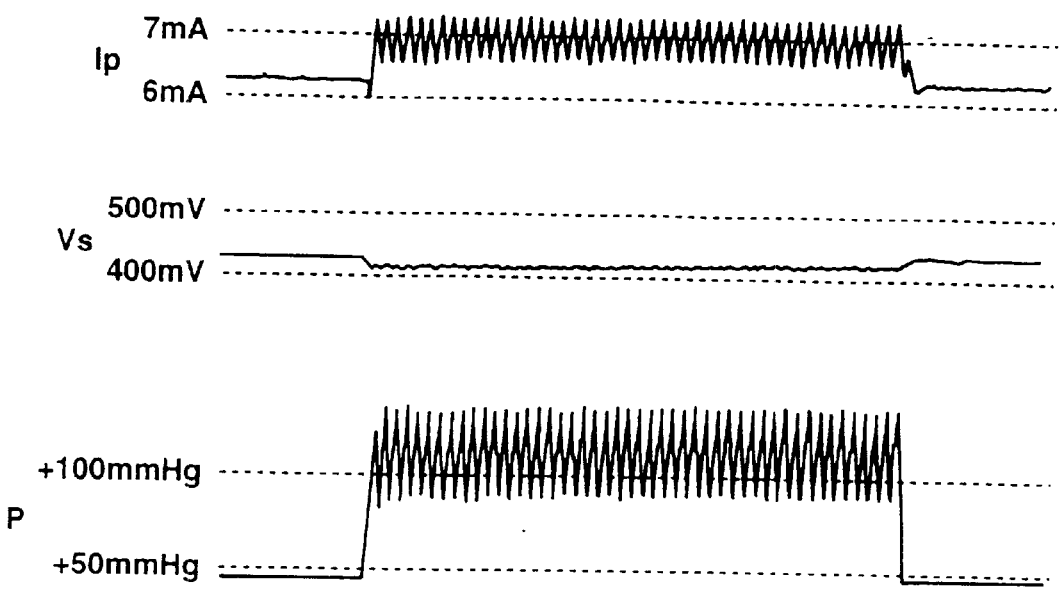
FIGS. 5A and 5B are views showing waveforms of pump current and output voltage of oxygen concentration cell element.

FIG. 5A is a graph showing the waveforms of the pump current Ip of the oxygen pump element 6 and the output voltage Vs of the oxygen concentration cell element 4.

As seen from FIG. 5A, in this embodiment, the porous electrode 6b of the oxygen pump element 6 which was located on the measurement gap 10 side was changed to such one that had a lower activity for thereby changing the responsiveness in control of the pump current Ip, whereby the amplitude of oscillations of the pump current Ip which resulted from pulsations of the exhaust gas could be reduced to half.

In the meantime, since the condition of increasing the amplitude of oscillations of the Ip current (i.e., the condition of causing a hunting in control) differs depending upon the circuit used and the type of oxygen sensor, etc., so it is necessary to determine the electrode materials used, on the basis of those conditions suitably and experimentally.

Further, while in the above described embodiment, the material for the porous electrode 6b of the oxygen pump element 6 on the measurement gap side is changed, it will suffice to change, in place thereof, the material for the other electrode 6c of the oxygen pump element 6 or the materials for both of the electrodes 6b and 6c of the oxygen pump element 6.

Figure 5B:
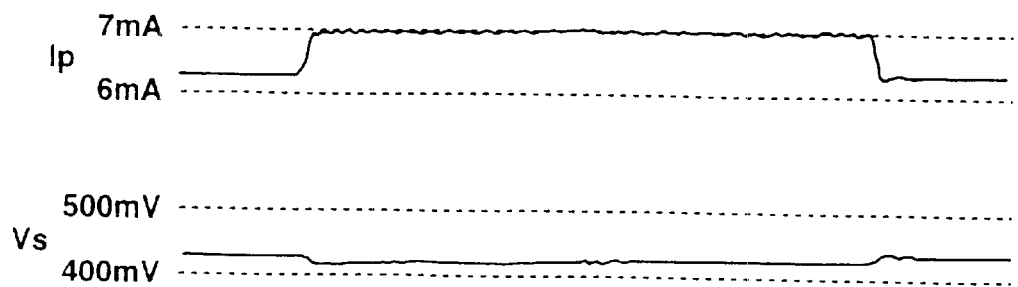

Further, in case the control which is carried out by using the result of detection of the oxygen concentration can be relatively low in the control speed, the pump current Ip is outputted through a low-pass filter so as to be used as an output signal of the oxygen sensor 2. In this case, as shown in FIG. 5B, the oscillations of the output signal can be reduced further, resulting in that the more accurate detection of the oxygen concentration can be attained.

In foregoing, it is to be noted that according to The present invention the oscillations of the pump current are reduced by adjusting the activity of the electrodes of the oxygen pump current and thereby changing the responsiveness in control of the pump current. That is, when the oscillation cycle of the pump current and the delay in control of the pump current have a particular relation to cause a hunting of the control of the pump current, the pump current which is the subject of the control is caused to oscillate. Further, the delay in control of the pump current is determined depending upon the delay due to a control by means of a control system circuit of itself and the delay due to a responsiveness in control of the pump current by means of the oxygen pump element. Accordingly, by adjusting the activity of the electrodes and thereby changing the responsiveness in control of the pump current in such a manner that the delay in the control of the pump current is set so as not to have the above described particular relation with the oscillation cycle of the pump current, increase of the oscillations of the pump current can be assuredly prevented. In the meantime, the activity of an electrode is herein used to indicate the likeliness of a chemical reaction (i.e., changing oxygen molecule into the form of ions or oxygen ions into the form of a molecule) between the solid electrolyte and the oxygen in the measured gas such as exhaust gas.

It is further to be noted that the larger interface at which oxygen, solid electrolyte and catalyst are simultaneously brought into contact with one another, the more improvement in the activity of the electrode, and the smaller interface the less improvement. Thus, adjustment of the activity can be attained through adjustment of the density of the solid electrolyte contained in the electrodes of the oxygen pump cell, or through adjustment of a quantity of a ceramic material contained in the electrodes of the oxygen pump element, which ceramic material is the same as that constituting the solid electrolyte base of the oxygen pump element.

It is further to be noted that for adjustment of the responsiveness in control of the pump current it will suffice to change at least one of the electrodes of the oxygen pump element. However, adjustment of the electrode on the measurement gap side and in contact with the measured gas is more effective. Thus, adjustment of one of the electrodes located on the measurement gap side is preferable.

While in the above described embodiment the present invention has been described and shown as being applied to an oxygen sensor, this is not for the purpose of limitation but the present invention can be applied to other gas sensors such as a nitrogen oxide sensor for detecting the concentration of NOx.

Many modifications and variations of the present invention are possible in light of the above teachings. Therefore, within the scope of the appended claims, the present invention may be practiced otherwise than as specifically described.

What is claimed is:

1. A method of stabilizing pump current in a gas sensor through suppression of oscillations of the pump current which result from pulsations of measured gas, the gas sensor including an oxygen pump element and an oxygen concentration cell element, each of which has a pair of porous electrodes containing a catalyst for accelerating a reaction between a solid electrolyte and oxygen and an oxygen ion conductive solid electrolyte base interposed between the electrodes, the gas sensor further including a measurement gap between the oxygen pump element and the oxygen concentration cell element and in communication with a measured gas side by way of a diffusion control layer, and operative to control the pump current through the oxygen pump element so that an output voltage of the oxygen concentration cell element is constant in order that an oxygen concentration in the measurement gap is maintained constant and detect an oxygen concentration in the measured gas on the basis of the pump current, the method comprising adjusting an activity of only one of said electrodes of said oxygen pump element with respect to the other one of said electrodes so as to change a responsiveness in control of said pump current and thereby reduce said oscillations of said pump current, wherein said adjusting comprises adjusting a density of a solid electrolyte contained in said electrodes of said oxygen pump element.

2. A method of stabilizing pump current in a gas sensor through suppression of oscillations of the pump current which result from pulsations of measured gas, the gas sensor including an oxygen pump element and an oxygen concentration cell element, each of which has a pair of porous electrodes containing a catalyst for accelerating a reaction between a solid electrolyte and oxygen and an oxygen ion conductive solid electrolyte base interposed between the electrodes, the gas sensor further including a measurement gap between the oxygen pump element and the oxygen concentration cell element and in communication with a measured gas side by way of a diffusion control layer, and operative to control the pump current through the oxygen pump element so that an output voltage of the oxygen concentration cell element is constant in order that an oxygen concentration in the measurement gap is maintained constant and detect an oxygen concentration in the measured gas on the basis of the pump current, the method comprising lowering an activity of only one of said electrodes of said oxygen pump element with respect to the other one of said electrodes to lower a responsiveness in control of said pump current and thereby reduce said oscillations of said pump current, wherein said lowering comprises adjusting a density of a solid electrolyte contained in said electrodes of said oxygen pump element.

* * * * *